United States Patent
Walsh

(10) Patent No.: US 6,660,884 B2
(45) Date of Patent: Dec. 9, 2003

(54) CATALYSTS, METHODS FOR MAKING SAID CATALYSTS, AND METHODS FOR MAKING CHIRAL COMPOUNDS WITH HIGH ENANTIOSELECTIVITY

(75) Inventor: Patrick J. Walsh, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 10/387,460

(22) Filed: Mar. 14, 2003

(65) Prior Publication Data

US 2003/0191345 A1 Oct. 9, 2003

Related U.S. Application Data

(60) Provisional application No. 60/364,883, filed on Mar. 14, 2002.

(51) Int. Cl.⁷ .................. C07C 303/40; C07C 311/25; C07C 29/78; C07C 29/40
(52) U.S. Cl. .................. 564/82; 568/810; 568/812; 568/813; 568/814
(58) Field of Search ............................ 564/82; 568/810, 568/812, 813, 814

(56) References Cited

U.S. PATENT DOCUMENTS 6,392,103 B1 * 5/2002 Mimoun .................. 568/814

OTHER PUBLICATIONS

Balsells, J.; Walsh, P. J. The Use of Achiral Ligands to Convey Asymmetry: Chiral Environment Amplification, J. Am. Chem. Soc. 2000, 122, 1802–1803.

Balsells, J.; Walsh, P. J. Design of Diastereomeric Self–Inhibiting Catalysts for Control of Turnover Frequency and Enantioselectivity, J. Am. Chem. Soc. 2000, 122, 3250–3251.

Dosa, P. I.; Fu, G. C. Catalytic Asymmetric Addition of ZnPh2 to Ketones: Enantioselective Formation of Quaternary Centers, J. Am. Chem. Soc. 1998, 120, 445–446.

Ramón, D. J.; Yus, M. The First Enantioselective Addition of Dialkylzinc to Ketones Promoted by Titanium(IV) Derivatives, Tetrahefron Lett. 1998, 39, 1239–1242.

Ramón, D. J.; Yus, M. First Enantioselective Addition of Diethylzinc and Dimethylzinc to Prostereogenic Ketones Catalysed by Camphorsulfonamide–Titanium Alkoxide Derivatives, Tetrahedron 1998, 54, 5651–5666.

* cited by examiner

*Primary Examiner*—Peter O'Sullivan
(74) *Attorney, Agent, or Firm*—Nath & Associates PLLC; Gary M. Nath; Lee C. Heiman

(57) ABSTRACT

The present invention relates to compounds useful as catalysts in asymmetric synthesis of chiral compounds, methods for the synthesis of said catalysts, and methods for synthesizing chiral compounds with high enantioselectivity.

11 Claims, No Drawings

US 6,660,884 B2

CATALYSTS, METHODS FOR MAKING SAID CATALYSTS, AND METHODS FOR MAKING CHIRAL COMPOUNDS WITH HIGH ENANTIOSELECTIVITY

This application claims the benefit of U.S. Provisional Patent Application No. 60/364,883, filed Mar. 14, 2002, the contents of which is hereby incorporated by reference in its entirety.

This work was supported in part by National Institutes of Health grant GM58101 and by National Science Foundation grant CHE-9733274. The United States government may have rights in this invention by virtue of this support.

BACKGROUND OF THE INVENTION

1. Field of Invention

The present invention relates to compounds useful as catalysts in asymmetric synthesis of chiral compounds, methods for the synthesis of said catalysts, and methods for synthesizing chiral compounds with high enantioselectivity.

2. Background

The addition of alkyl groups to ketones is a reaction that is so fundamental that it is studied in nearly all first year organic chemistry courses in this country. The lack of direct methods to perform this simple transformation enantioselectively represent a marked deficiency in prior organic methodology. We have developed a catalyst to promote the synthesis of tertiary alcohols with high enantioselectivity, which will be highly useful to chemists working in academics and industry.

The enantioselective formation of C—C bonds is an area of intense research effort. Traditionally, optimization of asymmetric catalysts has been performed by modification of chiral ligands. Some groups have used achiral additives to modify catalyst enantioselectivities and a few have used achiral ligands with chiral conformations to transfer asymmetry. We have developed asymmetric catalysts by variation of large, flexible achiral and meso ligands with chiral conformations.

Importance of Chiral Substances of High Optical Purity. Medications sold as single enantiomers comprise 50 of the 100 top selling drugs, and represent a $133 billion industry. The precursors of these medications are chiral substances of high optical purity, which constitute an important class of starting materials for organic and medicinal chemists. Using the stereochemistry of these materials to control generation of subsequent stereogenic centers allows the preparation of biologically and medicinally important target molecules as single enantiomers. Organic compounds of very high optical purity are essential for testing and evaluation of biological activity, because each enantiomer can interact with a distinct site in an organism and elicit very different responses.

Chemists and medical scientists have understood the significance of producing drugs as single enantiomers for many years. As chemists have honed their ability to generate chiral molecules and efficiently analyze their enantiopurity, the Food and Drug Administration ("FDA") has encouraged the pharmaceutical industry to introduce medications as single enantiomers. As a result of the FDA's actions, medications are increasingly being synthesized, tested, and sold as single enantiomers.

Historically, the production of medications as single enantiomers has been accomplished primarily by four different techniques: 1) use of natural sources as starting materials, 2) resolution of racemates, 3) chiral auxiliary chemistry, and 4) asymmetric catalysis. Increasingly, the use of chiral catalysts is displacing the application of chiral reagents and chiral auxiliaries in the asymmetric synthesis of natural and unnatural products. An active asymmetric catalyst enables the chemist to prepare large quantities of material with high enantiopurity from small amounts of enantiopure material, without the need to cleave and recover the chiral auxiliary. Despite recent advances in the art of asymmetric synthesis, many formidable challenges have remained. Significant among these has been the construction of chiral quarternary stereocenters, which are carbon centers with four different non-hydrogen substituents.

Asymmetric Synthesis of Tertiary Alcohols. Numerous attempts to accomplish asymmetric additions of alkyl groups to ketones have been reported, but few have been successful due to low enantioselectivities, high chiral ligand loadings, or extreme reaction conditions. Despite the fact that chemists have been studying the addition of organometallic reagents to ketones for almost 50 years, the catalytic asymmetric synthesis of complex molecules with tertiary alcohols has been one of the most challenging problems in chemical synthesis.

The chemistry of the prior art has not been practical because it was stoichiometric; it did not work with aryl, vinyl or alkynyl Grignard reagents; an excess of the reagent was needed to maximize enantioselectivity; and the reaction required very low temperature, below −100° C. The prior art reagents did not react, or reacted inefficiently, with ketones; new approaches are needed to address this important class of addition reactions.

Asymmetric Additions to Carbonyl Groups. In the catalytic asymmetric transfer of alkyl and aryl groups to carbonyls, aldehydes have served as suitable substrates. Literally hundreds of catalysts will now promote additions of zinc alkyl groups to aldehydes with excellent enantioselectivities. In sharp contrast, an effective use of ketones as alkyl group acceptors in the presence of asymmetric catalysts has not been described previously, reflecting the fact that ketones are significantly less susceptible to reaction with alkylzinc reagents than aldehydes. The best enantioselectivities achieved were in the range of 16% to 86%, which are not in the synthetically useful range. Further, a serious drawback to this methodology is the long reaction times of 4–14 days. Thus, while catalytic asymmetric addition of alkyl groups to ketones has been achieved, the prior art has had significant limitations and leaves much room for improvement.

The present invention relates to novel methods for the construction of C—C bonds with high asymmetric induction. One embodiment of this work is the generation of quarternary stereocenters with high enantioselectivity. Such centers are generally much more difficult to produce enantioselectively than secondary stereocenters, as evidenced by the limited examples of C—C bond formation with enantio- and diastereoselective nucleophilic addition to ketones. We employ chiral ligands as catalysts in asymmetric syntheses. Accordingly, Applicants have developed catalysts, methods for making said catalysts, and methods for using said catalysts in enantioselective alkylation of ketones.

SUMMARY OF THE INVENTION

The present invention relates to a compound selected from the group consisting of: Bicyclo[2.2.1]heptane-1-methanesulfonamide,N,N'-(1S,2S)-1,2-cyclohexanediylbis [2-hydroxy-7,7-dimethyl]-(1R,1'R,2S,2'S,4S,4'S)-(9CI) and Bicyclo[2.2.1]heptane-1-methanesulfonamide,N,N'-(1R, 2R)-1,2-cyclohexanediylbis[2-hydroxy-7,7-dimethyl]-(1S, 1'S,2R,2'R,4R,4'R)-(9CI).

The present invention further relates to a method for making a compound selected from the group consisting of: Bicyclo[2.2.1]heptane-1-methanesulfonamide,N,N'-(1S, 2S)-1,2-cyclohexanediylbis[2-hydroxy-7,7-dimethyl]-(1R, 1'R,2S,2'S,4S,4'S)-(9CI) and Bicyclo[2.2.1]heptane-1-methanesulfonamide,N,N'-(1R,2R)-1,2-cyclohexanediylbis[2-hydroxy-7,7-dimethyl]-(1S,1'S,2R,2'R,4R,4'R)-(9CI), comprising the steps of:

(a) reducing an enantiomer of 1,2-bis (camphorsulfonamido)-cyclohexane; and (b) separating said compound from the reaction mixture and its diastereoisomer.

In addition, the present invention relates to a method for making a chiral tertiary alcohol with high enantioselectivity, comprising reacting a metal-alkyl donor compound with a starting ketone compound in the presence of titanium(IV) isopropoxide and a compound selected from the group consisting of: Bicyclo[2.2.1]heptane-1-methanesulfonamide,N,N'-(1S,2S)-1,2-cyclohexanediylbis[2-hydroxy-7,7-dimethyl]-(1R,1'R,2S,2'S,4S,4'S)-(9CI) and Bicyclo[2.2.1]heptane-1-methanesulfonamide,N,N'-(1R, 2R)-1,2-cyclohexanediylbis[2-hydroxy-7,7-dimethyl]-(1S, 1'S,2R,2'R,4R,4'R)-(9CI).

DETAILED DESCRIPTION OF THE INVENTION

Definitions

The term "Bicyclo[2.2.1]heptane-1-methanesulfonamide, N,N'-(1S,2S)-1,2-cyclohexanediylbis[2-hydroxy-7,7-dimethyl]-(1R,1'R,2S,2'S,4S,4'S)-(9CI)", CAS Registry Number: 470665-33-9, refers to compound B, also referred to as "L*", as used herein:

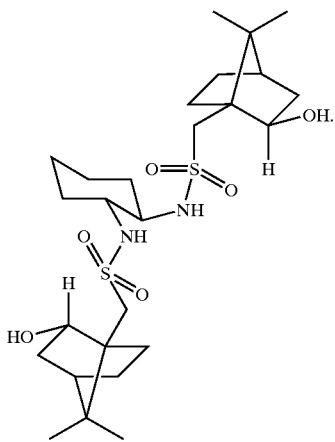

Similarly, the term "Compound B enantiomer" refers to the compound Bicyclo[2.2.1]heptane-1-methanesulfonamide, N,N'-(1R,2R)-1,2-cyclohexanediylbis[2-hydroxy-7,7-dimethyl]-(1S,1'S,2R,2'R,4R,4'R)-(9CI), CAS Registry Number: 470665-30-6.

The term "isomers" refers to different compounds that have the same molecular formula.

The term "stereoisomers" refers to isomers that differ only in the way the atoms are arranged in space, i.e. compounds that have the same atomic constitution, but a different arrangement of atoms.

The term "enantiomers" refers to a pair of stereoisomers that are non-superimposable mirror images of each other.

The terms "diastereoisomers" and "diastereomers" refer to stereoisomers which are not mirror images of each other.

The term "racemic mixture" refers to a mixture containing equal parts of individual enantiomers.

The term "non-racemic mixture" refers to a mixture containing unequal parts of individual enantiomers or stereoisomers.

The term "catalyst" refers broadly to a compound which produces or increases the rate of a chemical reaction, while itself remaining unchanged by the reaction.

DEVELOPMENT OF A CATALYTIC ASYMMETRIC SYNTHESIS OF CHIRAL TERTIARY ALCOHOLS

The addition of alkyl groups to ketones is a reaction that is so fundamental that it is studied in nearly all first year organic chemistry courses in this country. The lack of direct methods to perform this simple transformation enantioselectively represent a marked deficiency in prior organic methodology. We have developed a catalyst to promote the synthesis of tertiary alcohols with high enantioselectivity, which will be highly useful to chemists working in academics and industry.

Importance of Chiral Substances of High Optical Purity. Medications sold as single enantiomers comprise 50 of the 100 top selling drugs, and represent a $133 billion industry. The precursors of these medications are chiral substances of high optical purity, which constitute an important class of starting materials for organic and medicinal chemists. Using the stereochemistry of these materials to control generation of subsequent stereogenic centers allows the preparation of biologically and medicinally important target molecules as single enantiomers. Organic compounds of very high optical purity are essential for testing and evaluation of biological activity, because each enantiomer can interact with a distinct site in an organism and elicit very different responses.

Chemists and medical scientists have understood the significance of producing drugs as single enantiomers for many years. As chemists have honed their ability to generate chiral molecules and efficiently analyze their enantiopurity, the Food and Drug Administration ("FDA") has encouraged the pharmaceutical industry to introduce medications as single enantiomers. As a result of the FDA's actions, medications are increasingly being synthesized, tested, and sold as single enantiomers.

Historically, the production of medications as single enantiomers has been accomplished primarily by four different techniques: 1) use of natural sources as starting materials, 2) resolution of racemates, 3) chiral auxiliary chemistry, and 4) asymmetric catalysis. Increasingly, the use of chiral catalysts is displacing the application of chiral reagents and chiral auxiliaries in the asymmetric synthesis of natural and unnatural products. An active asymmetric catalyst enables the chemist to prepare large quantities of material with high enantiopurity from small amounts of enantiopure material, without the need to cleave and recover the chiral auxiliary. Despite recent advances in the art of asymmetric synthesis, many formidable challenges have remained. Significant among these has been the construction of chiral quarternary stereocenters, which are carbon centers with four different non-hydrogen substituents. The catalytic enantioselective generation of chiral quarternary centers has been a principal objective of Applicants' work.

The present invention thus relates to novel methods for the construction of C—C bonds with high asymmetric induction. One embodiment of this work is the generation of quarternary stereocenters with high enantioselectivity. Such centers are generally much more difficult to produce enantioselectively than secondary stereocenters as evidenced by the limited examples of C—C bond formation with enantio- and diastereoselective nucleophilic addition to ketones. The inventive subject matter provides catalysts, methods for making said catalysts, and methods for using said catalysts in the synthesis chiral molecules with high enantioselectivity.

We have developed catalysts, methods for making said catalysts, and methods for using said catalysts in enantioselective alkylation of ketones. More particularly, Applicants have developed a method for catalytic asymmetric synthesis of chiral tertiary alcohols.

Compounds of the Present Invention

The catalysts provided by the inventive subject matter are based on a trans-1,2-diaminocyclohexane diamine backbone and chiral camphor sulfonyl chlorides. Reaction of these reagents provides a bis(sulfonamide) dione compound, A, or its enantiomer, as depicted in Scheme 1. Reduction of the dione compound A, for example, provides the secondary diol, compound B, also as depicted in Scheme 1. Sodium borohydride is used as the reducing agent, giving a 3.5-1 ratio of the $C_2$-symmetric desired compound B to the $C_1$-symmetric product with both endo and exo hydroxyl groups. Our optimized yield for this reaction is 71%. Dione compound A has been made on a 50 g scale, and compound B has been prepared on a 7 g scale. Characterization of the ligand by 2D-NMR and X-ray crystallography confirms the expected structure. Thus, the present invention relates to a compound selected from the group consisting of: Bicyclo[2.2.1]heptane-1-methanesulfonamide,N,N'-(1S,2S)-1,2-cyclohexanediylbis[2-hydroxy-7,7-dimethyl]-(1R,1'R,2S,2'S,4S,4'S)-(9CI) and Bicyclo[2.2.1]heptane-1-methanesulfonamide,N,N'-(1R,2R)-1,2-cyclohexanediylbis[2-hydroxy-7,7-dimethyl]-(1S,1'S,2R,2'R,4R,4'R)-(9CI).

Methods for Making a Highly Enantioselective Catalyst

The present invention further relates to a method for making a compound selected from the group consisting of: Bicyclo[2.2.1]heptane-1-methanesulfonamide,N,N'-(1S,2S)-1,2-cyclohexanediylbis[2-hydroxy-7,7-dimethyl]-(1R,1'R,2S,2'S,4S,4'S)-(9CI) and Bicyclo[2.2.1]heptane-1-methanesulfonamide,N,N'-(1R,2R)-1,2-cyclohexanediylbis[2-hydroxy-7,7-dimethyl]-(1S,1'S,2R,2'R,4R,4'R)-(9CI), comprising the steps of:

(a) reducing an enantiomer of 1,2-bis(camphorsulfonamido)-cyclohexane; and (b) separating said compound from the reaction mixture and its diastereoisomer.

In a preferred embodiment, the step of reducing said intermediate is carried out at room temperature in a reaction mixture additionally comprising sodium borohydride in a 1:1 mixture of isopropyl alcohol and tetrahydrofuran.

In another preferred embodiment, the step of separating said compound from its diastereoisomer is carried out by column chromatography.

In a further preferred embodiment, the method comprises the additional steps, following the step of reducing said intermediate and preceding the step of separating said compound from the reaction mixture and its diastereoisomer, of:

(i) quenching the reaction mixture; and (ii) recovering said compound.

One of ordinary skill in the art will recognize that the step of recovering a compound from a reaction mixture involves such exemplary steps as removing solvent(s) from the reaction mixture; washing the reaction mixture in aqueous solution(s) and/or organic solvents(s); and combining, drying, extracting, and concentrating aqueous and organic fractions, as appropriate to the reaction type. One of ordinary skill in the art will further recognize that the particular reagents, solvents, equipment, and procedures to be used in the recovery process are employed in the discretion of the skilled artisan, with many options available as to the selection of the reagents, solvents, equipment, and procedures to be utilized.

The compound of the present invention may be readily prepared by standard techniques of organic chemistry, utilizing readily available reagents and the synthetic pathway depicted below.

In the preparation of the compounds of the invention or their precursors, one skilled in the art will understand that one may need to protect or block various reactive functionalities on the starting compounds or intermediates while a desired reaction is carried out on other portions of the molecule. After the desired reactions are complete, or at any desired time, normally such protecting groups will be removed by, for example, hydrolytic or hydrogenolytic means. Such protection and deprotection steps are conventional in organic chemistry. One skilled in the art is referred to "Protective Groups in Organic Chemistry," McOmie, ed., Plenum Press, New York, N.Y.; and "Protective Groups in Organic Synthesis," Greene, ed., John Wiley & Sons, New York, N.Y. (1981) for the teaching of protective groups which may be useful in the preparation of compounds of the present invention.

The product and intermediates may be isolated or purified using one or more standard purification techniques, including, for example, one or more of simple solvent evaporation, recrystallization, distillation, sublimation, filtration, chromatography, including thin-layer chromatography, HPLC (e.g. reverse phase HPLC), column chromatography, flash chromatography, radial chromatography, trituration, and the like.

SCHEME 1

As depicted by exemplary Scheme 1, the compounds of the inventive subject matter are based on trans-1,2-diaminocyclohexane and camphor sulfonyl chloride, both of which are commercially available. Reaction of these reagents in the presence of $Et_3N$ provides a diketone intermediate 1,2-bis(camphorsulfonamido)-cyclohexane, either as exemplary Compound A or its enantiomer. Methods for the preparation of the intermediate are known in the art.

A diketone intermediate was reduced with $NaBH_4$ to form two diastereomers in a 3.5:1 ratio. The diastereomers were easily separated by chromatography on silica. The major diastereomer, isolated in 71% yield, was shown by 2D NMR to be a $C_2$-symmetric diol, compound B, Bicyclo[2.2.1]heptane-1-methanesulfonamide,N,N'-(1S,2S)-1,2-cyclohexanediylbis[2-hydroxy-7,7-dimethyl]-(1R,1'R,2S,2'S,4S,4'S)-(9CI). This two-step synthetic process, as depicted below in Scheme 1, has been used to prepare 6.7 g (12.2 mmol) of compound B, which is an efficient and highly enantioselective catalyst for the addition of alkyl groups to ketones.

SCHEME 1

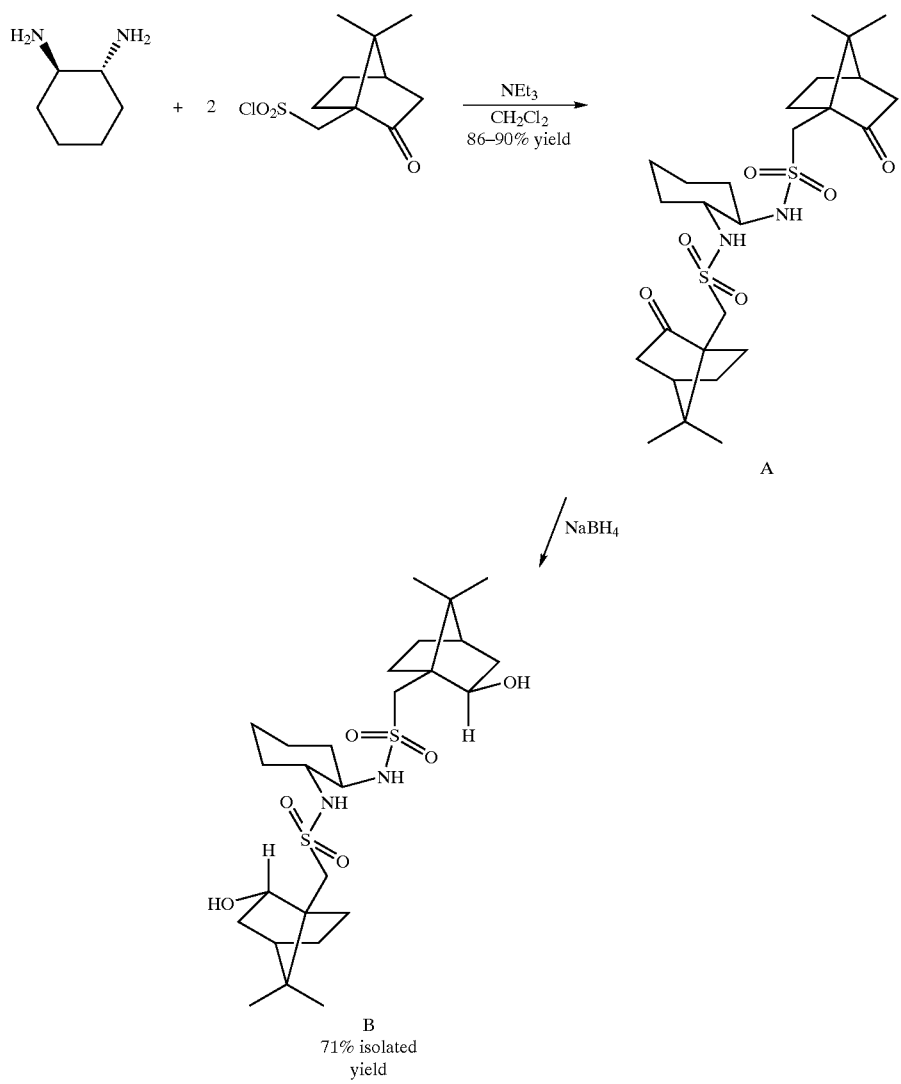

Methods for Making Highly Enantioenriched Compounds

In addition, the present invention relates to a method for making a chiral tertiary alcohol with high enantioselectivity, comprising reacting a metal-alkyl donor compound with a starting ketone compound in the presence of titanium(IV) isopropoxide and a compound selected from the group consisting of: Bicyclo[2.2.1]heptane-1-methanesulfonamide,N,N'-(1S,2S)-1,2-cyclohexanediylbis[2-hydroxy-7,7-dimethyl]-(1R,1'R,2S,2'S,4S,4'S)-(9CI) and Bicyclo[2.2.1]heptane-1-methanesulfonamide,N,N'-(1R,2R)-1,2-cyclohexanediylbis[2-hydroxy-7,7-dimethyl]-(1S,1'S,2R,2'R,4R,4'R)-(9CI).

In a preferred embodiment, said metal-alkyl donor compound is dialkylzinc.

In a more preferred embodiment, said metal-alkyl donor compound is diethylzinc.

In another preferred embodiment, said starting ketone compound is of Formula II:

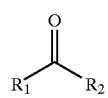

wherein:
- $R_1$ and $R_2$ are independently selected from the group consisting of straight or branched $C_1$–$C_9$ alkyl, straight or branched $C_2$–$C_9$ alkenyl, straight or branched $C_2$–$C_9$ alkynyl, straight or branched $C_1$–$C_9$ alkyl substituted at one or more positions with Ar, straight or branched $C_2$–$C_9$ alkenyl substituted at one or more positions with Ar, and straight or branched $C_2$–$C_9$ alkynyl substituted at one or more positions with Ar,
- or $R_1$ and $R_2$ are taken together to form a 5–7 membered alicyclic or aromatic, carbo- or heterocyclic ring; and
- Ar is an aromatic, mono-, bi- or tricyclic, carbo- or heterocyclic ring, wherein the ring is optionally substituted with one or more substituent(s) independently selected from the group consisting of alkylamino, amido, amino, aminoalkyl, azo, benzyloxy, $C_1$–$C_9$ straight or branched chain alkyl, $C_1$–$C_9$ alkoxy, $C_2$–$C_9$ alkenyloxy, $C_2$–$C_9$ straight or branched chain alkenyl, $C_3$–$C_8$ cycloalkyl, $C_5$–$C_7$ cycloalkenyl, carbonyl, carboxy, cyano, diazo, ester, formanilido, halo, haloalkyl, hydroxy, imino, isocyano, isonitrilo, nitrilo, nitro, nitroso, phenoxy, sulfhydryl, sulfonylsulfoxy, thio, thioalkyl, thiocarbonyl, thiocyano, thioester, thioformamido, trifluoromethyl, and carboxylic and heterocyclic moieties; wherein each individual alicyclic or aromatic ring contains 5–8 members and wherein each heterocyclic ring contains 1–6 heteroatom(s) independently selected from the group consisting of O, N, and S.

In a more preferred embodiment, said starting ketone compound is a straight or branched $C_1$–$C_9$ alkyl ketone, a straight or branched $C_1$–$C_9$ alkyl aryl ketone, or a straight or branched $C_1$–$C_9$ α,β-unsaturated ketone which is optionally substituted with Ar.

In a more preferred embodiment, said method comprises the additional step of isolating the resulting chiral tertiary alcohol.

Compound B can be prepared on multi-gram scale in two steps from commercially available materials. We have developed this new catalyst for the enantioselective allylation of ketones. Many catalysts will promote the allylation of aldehydes, but only two are reactive enough to allylate ketones. We observe enantioselectivities in the 90% range with most aromatic ketones and α,β-unsaturated ketones. Our catalyst is the most enantioselective and efficient developed to date, promoting enantioselective synthesis at concentrations as low as 0.5 mol %. Considerable substrate generality has been demonstrated in our work with compound B. Compound B is an efficient and highly enantioselective catalyst for the addition of alkyl groups to ketones, as shown in Scheme 2.

SCHEME 2

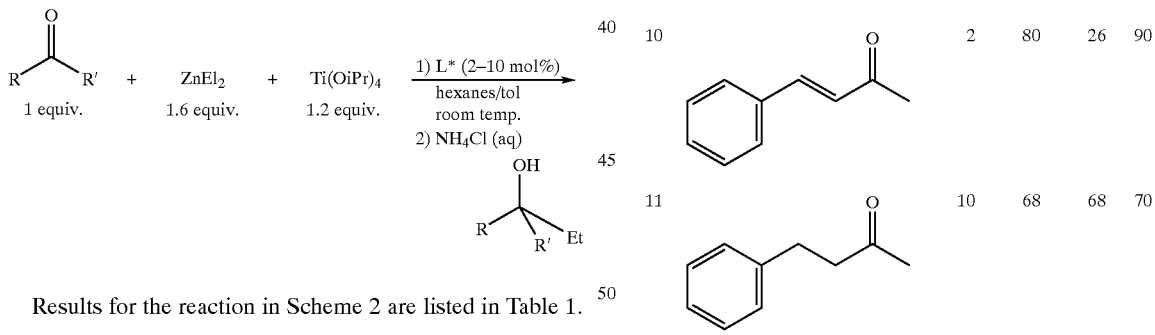

Results for the reaction in Scheme 2 are listed in Table 1.

TABLE 1

| entry | | mol % | yield | time (h) | $ee^2$ (config) |
|---|---|---|---|---|---|
| 1 | X = H | 2 | 71 | 29 | 96 (S) |
| 2 | X = 3-Me | 10 | 82 | 12 | 99 |
|   |          | 2  | 78 | 24 | 99 |
| 3 | X = 4-OMe | 10 | 85 | 111 | 94 |
| 4 | X = 3-$CF_3$ | 2 | 56 | 14 | 98 |

TABLE 1-continued

| entry | | mol % | yield | time (h) | $ee^2$ (config) |
|---|---|---|---|---|---|
| 5 | X = 2-Me | 10 | 24 | 48 | 96 |
| 6 | (α-tetralone) | 10 | 35 | 22 | >99 |
| 7 | (PhC(O)Bu) | 10 | 83 | 47 | 87 |
|   |   | 2 | 79 | 102 | 88 |
| 8 | (PhC(O)CH₂CH₂Cl) | 10 | 82 | 44 | 89 |
| 9 | (1-acetylcyclohexene) | 2 | 56 | 46 | 96 |
| 10 | (benzalacetone) | 2 | 80 | 26 | 90 |
| 11 | (PhCH₂CH₂C(O)CH₃) | 10 | 68 | 68 | 70 |

Asymmetric Synthesis of Tertiary Alcohols. The simplest method for the asymmetric synthesis of tertiary alcohols would seem to be the addition of organometallic reagents to ketones. In theory, this approach simultaneously generates a quarternary stereocenter, a C—C bond, and a hydroxyl group, the latter of which has proven to be an excellent directing group in subsequent diastereoselective steps. Numerous attempts to accomplish asymmetric additions of alkyl groups to ketones have been reported, but few have been successful due to low enantioselectivities, high chiral ligand loadings, or extreme reaction conditions. Despite the fact that chemists have been studying the addition of organometallic reagents to ketones for almost 50 years, the catalytic asymmetric synthesis of complex molecules with tertiary alcohols has been one of the most challenging problems in chemical synthesis.

Initial studies into the asymmetric addition of alkyl groups to ketones were reported in 1953 using Grignard reagents in the presence of a chiral solvent, (S,S)-2,3-dimethoxybutane. Enantioselectivities of around 5% were obtained. Many other chiral ligands have been used over the years with little success. It was not until 1992 that the first stoichiometric asymmetric addition of alkyl groups to ketones with high enantioselectivity were developed (Weber, B., Seebach, D. *Enantiomerically Pure Tertiary Alcohols by TADDOL-Assisted Additions to Ketones-or How to Make a Grignard Reagent Enantioselective*, Angew. Chem., Int. Ed., 31:84–86 (1992) and Weber, B., Seebach, D. *Ti-TADDOLate-Catalyzed, Highly Enantioselective Addition of Alkyl-and Aryl-titanium Derivatives to Aldehydes*, Tetrahedron, 50:7473–7484 (1994)). However, the chemistry was not practical because it was stoichiometric in the quantity of TADDOL; it did not work with aryl, vinyl or alkynyl Grignard reagents; an excess of the Grignard reagent was needed to maximize enantioselectivity; and the reaction required very low temperature, below −100° C.

To circumvent the high reactivity of organolithium and organomagnesium reagents with aldehydes, dialkylzinc reagents, which react very slowly with aldehydes in the absence of ligands, have also been used. In the presence of amino alcohol ligands, alkylzinc species efficiently add to aldehydes, giving secondary alcohols with excellent enantioselectivity. Unfortunately, dialkylzinc reagents did not react with ketones, and new approaches were needed to address this important class of addition reactions.

Asymmetric Additions to Carbonyl Groups. In the catalytic asymmetric transfer of alkyl and aryl groups to carbonyls, aldehydes have served as suitable substrates. Literally hundreds of catalysts will now promote additions of zinc alkyl groups to aldehydes with excellent enantioselectivities. In sharp contrast, the use of ketones as alkyl and aryl group acceptors in the presence of asymmetric catalysts had been described only twice before our development of the inventive subject matter. The lack of reports on catalytic asymmetric additions to ketones reflects the fact that ketones are significantly less susceptible to reaction with alkylzinc reagents than aldehydes. For example, titanium-based catalysts involving bis (sulfonamide), TADDOL, and BINOL ligands have been shown to give high enantioselectivity for the asymmetric addition of alkyl groups to aldehydes but do not promote analogous additions to ketones.

For example, the addition of diethylzinc to ketones in the presence of certain camphor sulfonamide derivatives was found to generate a somewhat more enantioselective and active catalyst. However, the best enantioselectivities achieved were in the range of 16% to 86%, the majority of which are not in the synthetically useful range. Further, a serious drawback to this methodology is the reaction time of 4 days to 14 days. Thus, while the first catalytic asymmetric addition of alkyl groups to ketones had been achieved, it has significant limitations and leaves much room for improvement. We have developed a catalyst for this reaction that is significantly more active and more enantioselective.

Acetophenone and related derivatives are excellent substrates for this catalyst. Reaction of acetophenone is complete after 24 h and the addition product is formed in 97% enantiomeric excess ("ee"). Electron donating and withdrawing substituents have little effect on the ee of the product, with the 3-$CF_3$ and 4-OMe acetophenones giving 92 and 94% ee, respectively.

There is, however, a significant electronic effect on the rate of the reaction. The 3-trifluoromethyl derivative is complete in 14 hours, and the 4-methoxyacetophenone requires 111 hours. This suggests that the rate-determining step is the asymmetric addition and not the liberation of the substrate from the catalyst. It is of note that under the optimized reaction conditions, catalyst loading can be dropped to 2 mol % with reaction times of 24 hours. We have employed as little as 0.5 mol % compound B and observed only a small 3% drop in ee. This low ligand loading is unusual for early transition metal catalysts. Alkyl aryl ketones such as valerophenone and 3-chloropropiophenone gave slightly lower enantioselectivities of 87 and 89% ee, respectively. Ethyl addition to α-tetralone produced>99% enantioselectivity; however, the yield is relatively low as a result of the competitive aldol/dehydration sequence.

α,β-Unsaturated Ketones. α,β-Unsaturated ketones are an important class of substrates for this asymmetric addition reaction, because the products are allylic alcohols. The hydroxyl group of the allylic alcohol product can be used to direct subsequent transformations of the double bond. Among the α,β-unsaturated ketones, trans-4-Phenyl-3-butene-2-one was envisioned to be a difficult substrate because the size of the methyl and vinyl groups are comparable. Nonetheless, this substrate underwent reaction with 90% ee. Surprisingly, 4-phenyl-2-butanone, produced 70% ee, indicating that the catalyst differentiates between methyl and methylene with reasonable success. 3-methylaceophenone underwent addition on a 37 mmol scale to provide the product with 99% ee in 78% yield (2 mol % catalyst loading, 24 hours, room temperature). Our asymmetric addition catalyst represents a significant advance and is the first and only practical catalyst for the enantioselective addition of alkyl groups to ketones.

Cyclic Enones. α,β-substituted conjugated cyclic enones are of significant interest because the resulting tertiary allylic alcohols are valuable intermediates. Unlike 2-cyclohexenone, the lone pairs are easily differentiated; based on results with α-tetralone (>99% ee), these substrates are expected undergo addition with high enantioselectivities, according to the reaction depicted in Scheme 3.

SCHEME 3

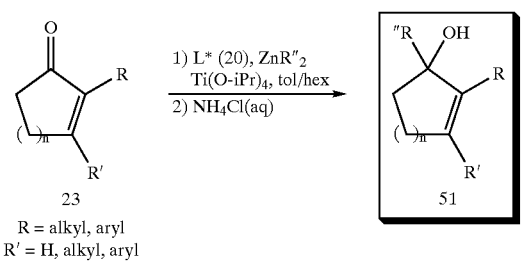

R = alkyl, aryl
R' = H, alkyl, aryl

A tertiary allylic alcohol product can be transformed into a number of highly functionalized compounds, as shown in Scheme 4.

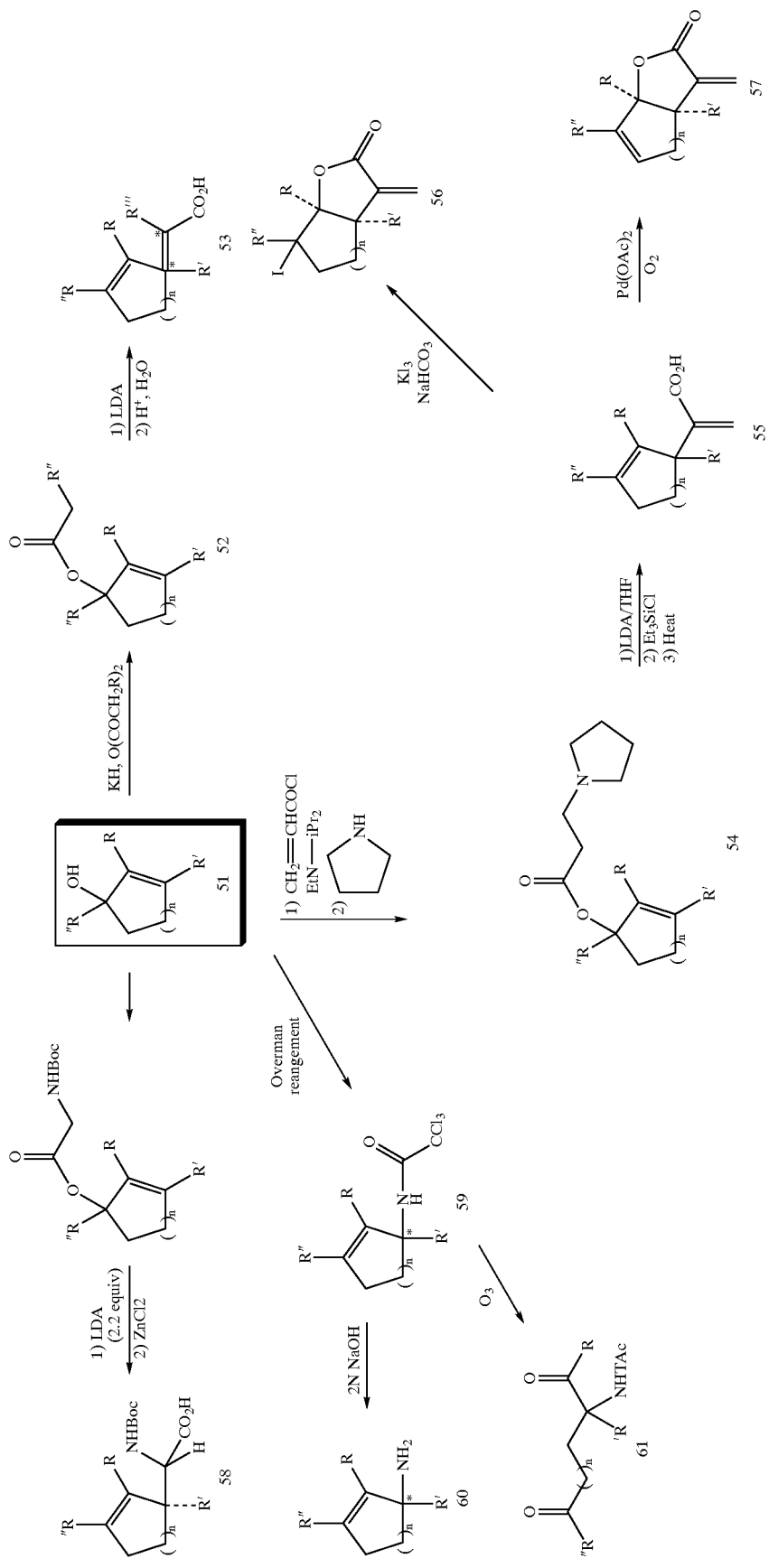

Allylic tertiary alcohols are ideal for further elaboration via [3,3]-sigmatropic rearrangements. Such reactions have been explored extensively with primary and secondary allylic alcohol derivatives. Further, compared to primary and secondary allylic esters, tertiary allylic esters have received little attention in the Ireland-Claisen rearrangement. This observation has been rationalized by lack of methods for the asymmetric synthesis of tertiary allylic alcohols. Deprotonation of a tertiary allylic ester will induce the Ireland-Claisen rearrangement to give a carboxylic acid with conservation of enantiomeric excess.

Another area of interest is the synthesis of α-methylene-γ-butyrolactone derivatives. These compounds show cytotoxic, antitumoral, and bactericidal properties that have been attributed to their ability to act as Michael acceptors with biological nucleophiles such as L-cysteine or thio-containing enzymes. Use of tertiary allylic alcohols synthesized by our methods will facilitate access to precursors in the enantioselective synthesis of these biologically important compounds. Using a pyrrolidine modified ester enolate Claisen procedure, deprotonation and rearrangement of leads to an intermediate which can be cyclized by an iodiolactonization reaction or with Pd(OAc)$_2$ under oxygen to provide α-methylene-γ-butyrolactones.

The rapid assembly of complex allylic amines and amino acids with high enantioselectivity has been a difficult task. The chiral tertiary allylic alcohols described above are also good candidates for conversion to non-proteinogenic α-amino acids. Such compounds are accessible from chiral tertiary allylic alcohols as described in Scheme 4. Further, application of an imidate rearrangement reaction is expected to provide an allylic amine protected as a trichloroacetate. In some cases, a rearrangement gives low yields when the reaction generates a quaternary center bound to nitrogen, but these substrates give good yields when trifluoroacetonitrile is employed. The trichloro- and trifluoroacetate protecting groups of the rearranged products are easily removed with mild base in methanol at room temperature to give the final product. As illustrated in Scheme 4, the protected allylic amines can also be oxidatively cleaved. Due to the prior difficulty preparing tertiary allylic alcohols with high enantioselectivity, such compounds as are shown in Scheme 4 have been infrequently used in this chemistry.

Additions of alkyl groups to α,β-unsaturated Ynones produce propargylic alcohols. These compounds can in turn provide access to E- or Z-allylic alcohols by reduction of the alkyne. Both allylic alcohols and propargylic alcohols are useful building blocks for a host of transformations.

Addition of Alkynes to Ketones. The asymmetric addition of alkynylzinc reagents to aldehydes is a useful method for the production of chiral secondary propargylic alcohols, which are valuable building blocks. The use of Zn(OTf)$_2$ and amine bases to generate alkynylzinc complexes that undergo addition to aldehydes in the stoichiometric and catalytic enantioselective synthesis of secondary propargylic alcohols. This methodology fails with aryl aldehydes, and we are not aware of reports on the asymmetric addition of alkynylzinc reagents to ketones to give tertiary propargylic alcohols. We have completed two such additions involving the reaction of phenylacetylene with acetophenone and obtained product in a promising 90% ee with compound B. Surprisingly, the high ee was obtained in THF, a solvent in which Lewis acidic catalysts typically do not function because of its ability to inhibit the catalyst by coordination. We expect that a catalytic amount of Zn(OTf)$_2$ and Et$_3$N will produce formation of the zinc acetylide, followed by asymmetric addition and proton transfer to the product to generate the tertiary alcohol product (see Schemes 5 and 6).

SCHEME 5

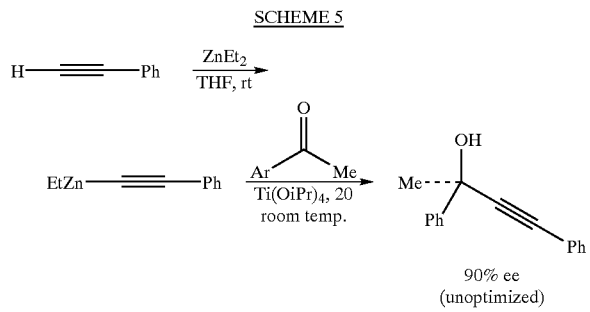

90% ee
(unoptimized)

SCHEME 6

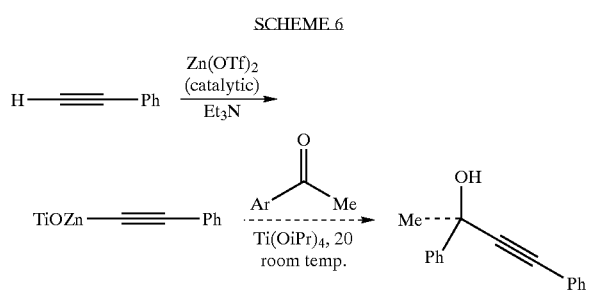

In summary, we have solved the difficult problem of the catalytic enantioselective addition of alkyl groups to ketones. Although hundreds of catalysts will promote the addition of alkyl groups to aldehydes, only our catalyst will promote the efficient and highly enantioselective additions to ketones, with ee's over 90% in most cases. We expect that the scope of the additions to ketones may be expanded by employing functionalized alkyl groups to prepare a wide variety of chiral building blocks with high enantioselectivity.

Our work to date indicates that the inventive catalyst also promotes the asymmetric addition of vinyl, phenyl, and alkynyl groups to ketones with excellent unoptimized enantioselectivities of over 85%. The catalytic asymmetric addition of vinyl and alkynyl groups to ketones has not been previously described to our knowledge, but will allow access to valuable materials that are currently difficult to prepare.

Examples of some compounds produced with high enantioselectivity using the inventive compound and methods may be found in Examples 2–12 below.

EXAMPLES

The following examples are illustrative of the present invention and are not intended to be limitations thereon. Unless otherwise indicated, all percentages are based upon 100% by weight of the final composition.

Example 1

Preparation of Compound B

The following example illustrates the preparation of compound B as provided according to the present invention.

The Bis (sulfonamide) dione, compound A (12 g, 22 mmol, 1.0 equiv) was charged to the reaction vessel with a 1:1 mixture of isopropyl alcohol and THF (400 mL). Compound A was only partially soluble in this mixture. NaBH$_4$ (5.8 g, 150 mmol, 6.9 equiv) was added portionwise over 5 minutes, and the turbid gray mixture quickly became homogeneous. The reaction mixture was stirred until the foaming subsided (about 0.5 h), then quenched carefully with saturated NH$_4$Cl (70 mL). The organic solvents were removed from the two-phase mixture under reduced pressure. Dichloromethane (100 mL) was added to the resulting aqueous mixture, then the organic layer was separated from the aqueous layer and washed with H$_2$O (2×20 mL). The aqueous fractions were combined and extracted with CH$_2$Cl$_2$ (2×50 mL). The organic fractions were combined, dried over Na$_2$SO$_4$, and concentrated to give 12 g of white foam. The diastereomers were separated by column chromatography (hexanes/EtOAc: 70/30) to yield 6.7 g (55%) of Compound B and 1.93 g (16%) of its diastereomer, a ratio of 3.5:1.

Data for Compound B: mp 181.5–182.3° C.; [α]D 20=−34.4 (c 3.0, CH$_2$Cl$_2$); 1H NMR (CDCl$_3$, 500 MHz) δ 0.84 (s, 6H), 1.07 (s, 6H), 1.08–1.2 (m, 2H), 1.26–1.43 (m, 4H), 1.43–1.56 (m, 2H), 1.66–1.88 (m, 12H), 2.09–2.21 (m, 2H), 2.92 (d, J=13.6 Hz, 2H), 3.05–3.12 (m, 2H), 3.32 (d, J=3.5 Hz, 2H), 3.50 (d, J=13.6 Hz, 2H), 4.01–4.12 (m, 2H), 5.07 (d, J=7.3 Hz, 2H) ppm; 13C{1H} NMR (CDCl$_3$, 125 MHz) δ 20.3, 20.9, 25.1, 27.7, 31.0, 35.1, 39.5, 44.9, 49.2, 51.0, 53.8, 54.4, 58.1 ppm; IR (KBr) 3528, 3298, 2938, 1456, 1390, 1372, 1319, 1146, 1075, 1058, 1028, 982, 903, 771, 701, 580 cm−1; HRMS calcd for C$_{26}$H$_{46}$N$_2$O$_6$S$_2$Na (M+Na)+: 569.2695, found 569.2668.

In addition, the enantiomer of Compound B, Bicyclo [2.2.1]heptane-1-methanesulfonamide,N,N'-(1R,2R)-1,2-cyclohexanediylbis[2-hydroxy-7,7-dimethyl]-(1S,1'S,2R,2'R,4R,4'R)-(9CI), was also prepared, by the same method as described in Example 1, except that the opposite enantiomer of the starting materials was used.

General Procedures

Conditions for the Determination of Enantiomeric Excess. The racemic alcohols were prepared by addition of ethylmagnesium bromide to the corresponding ketone. The tertiary alcohols 1, 2, 4–7, and 9 were analyzed by chiral capillary gas chromatograph ("GC"). The specifications for the GC analyses were as follows: Fused silica chiral capillary column (Supelco β-Dex 120): 30 m×0.25 mm (id)×0.25 μm film thickness. Carrier gas: nitrogen. Inlet temperature: 250° C. Detector: FID, 270° C. The conditions for the resolution of the racemates by GC are given below.

2-Phenyl-2-butanol (1). t1=25.8 min, t2=26.7 min (110° C., 1.0 mL/min).

2-(3-Methylphenyl)-2-butanol (2). t1=38.1 min, t2=40.6 min (105° C., 1.5 mL/min).

2-(3-Trifluoromethylphenyl)-2-butanol (4). t1=21.2 min, t2=22.7 min (110° C., 1.0 mL/min).

2-(2-Methylphenyl)-2-butanol (5). t1=47.3 min, t2=49.6 min (110° C., 1.0 mL/min).

1-Ethyl-1,2,3,4-tetrahydro-naphthalen-1-ol (6). t1=38.2 min, t2=41.9 min (125° C., 2.5 mL/min).

3-Phenyl-3-heptanol (7). t1=57.1 min, t2=59.5 min (110° C., 1.5 mL/min).

2-(1-Cyclohexenyl)-2-butanol (9). t1=20.8 min, t2=21.9 min (110° C., 1.0 mL/min).

Chiral HPLC analyses of 3, 8, 10 and 11 were performed using a Chiralcel OD-H column. The conditions for the resolution of the racemates are described below.

2-(4-Methoxyphenyl)-2-butanol (3). t1=23.7 min, t2=28.2 min (hexane/2-propanol: 99/1, 0.8 mL/min).

1-Chloro-3-phenyl-3-pentanol (8). t1=42.7 min, t2=53.2 min (hexane/2-propanol: 98/2, 0.7 mL/min).

(1E)-3-Methyl-1-phenyl-1-penten-3-ol (10). t1=25.8 min, t2=29.8 min (hexane/2-propanol: 95/5, 0.5 mL/min).

3-Methyl-1-phenyl-3-pentanol (11). t1=59.1 min, t2=64.7 min (Hexane/2-propanol: 99.4/0.6, 1.0 mL/min).

General Procedure A for Examples 2–12. Compound B (2–10 mol %) was weighed into the reaction vessel, and a diethylzinc solution (1.0 M toluene solution, 1.4–1.6 equiv) and titanium(IV) isopropoxide (1.4 M toluene solution, 1.2 equiv) were added at room temperature. After 5–10 min, the substrate ketone (1.0 equiv) was added neat. The homogeneous reaction mixture was stirred at room temperature. After completion, it was quenched with saturated aqueous solution NH$_4$Cl, extracted into CH$_2$Cl$_2$, concentrated under reduced pressure, and purified by column chromatography or column filtration.

General Procedure B for Examples 2–12. General Procedure A was followed, except that the substrate (a solid) was added as a solution in toluene.

Example 2

Preparation of 2-Phenyl-2-butanol (1)

A reaction with acetophenone (400 μL, 3.43 mmol) was performed according to general procedure A using 2 mol % (37.4 mg) of Compound B. Chromatography on neutral alumina (hexanes/EtOAc: 99/1) afforded 293 mg (71% yield, 96% ee, (S)) of a colorless oil: [α]D 20=−16.7 (c 0.72, Acetone). [Published [α]D 20=−15.9 (c 1.50, Acetone, 96% ee)].

Example 3

Preparation of 2-(3-Methylphenyl)-2-butanol (2)

The general procedure A was applied to 3-methylacetophenone on a 0.15 mL (1.09 mmol) scale, using 10 or 2 mol % of the Compound B enantiomer (60 or 12 mg, respectively). The crude was purified by column chromatography on silica gel (hexanes/EtOAc: 95/5) to give 2 (147 mg, 82.0% yield and 140 mg, 78% yield respectively, 99.0% ee) as an oil: [α]D 20=−4.08 (c 0.6, CHCl$_3$); 1H NMR (CDCl$_3$, 500 MHz) δ 0.71 (dd, J=7.4, 7.4 Hz, 3H), 1.44 (s, 3H), 1.73 (dq, J=7.4, 7.4, 7.4, 14.9 Hz, 1H), 1.76 (dq, J=7.4, 7.4, 7.4, 14.9 Hz, 1H), 2.27 (s, 3H), 6.95–6.97 (m, 1H), 7.11–7.17 (m, 3H) ppm; 13C{1H} NMR (CDCl$_3$, 125 MHz) δ 8.7, 22.0, 30.0, 37.0, 75.3, 122.3, 126.0, 127.6, 128.4, 138.0, 148.2 ppm; IR (NaCl) 3420, 2970, 1606, 1456, 1373, 1162 cm−1.

Example 4

Preparation of 2-(4-Methoxyphenyl)-2-butanol (3)

The general procedure A was applied to 4-methoxyacetophenone on a 112 mg (0.73 mmol) scale, using 10 mol % of Compound B (40 mg). The crude product was purified by column chromatography on silica gel (hexanes/EtOAc: 8/2) to give 3 (112 mg, 85.2% yield, 94.0% ee) as an oil: [α]D 20=−13.32 (c 1.8, CHCl$_3$); 1H NMR (CDCl$_3$, 500 MHz) δ 0.77 (dd, J=7.4, 7.4 Hz, 3H), 1.50 (s, 3H), 1.76–1.82 (m, 2H), 3.78 (s, 3H), 6.83–6.86 (m, 2H), 7.31–7.34 (m, 2H) ppm; 13C{1H} NMR (CDCl$_3$, 125 MHz) δ 8.8, 29.9, 37.1, 55.6, 75.0, 113.7, 126.5, 140.3, 158.5 ppm; IR (NaCl) 3444, 2967, 1610, 1300, 1179 cm−1; MS (m/z relative intensity) 180 (M)+ (7), 165 (MCH3)+ (5), 163 (—OH)+ (49), 162 (M-H2O) (15); HMRS calcd for $C_{11}H_{15}$(—OH)+: 163.1122, found 163.1129.

Example 5

Preparation of 2-(3-Trifluoromethylphenyl)-2-butanol (4)

The general procedure A was applied to 3-(trifluoromethyl)acetophenone on a 0.14 mL (0.91 mmol) scale, using 2 mol % of the Compound B enantiomer (10 mg). The crude was purified by neutral alumina column chromatography (hexanes/EtOAc: 9/1) to give 4 (107 mg, 55.5% yield, 98.0% ee) as an oil: [α]D 20=+8.82 (c 1.5, CHCl₃); 1H NMR (CDCl₃, 500 MHz) δ 0.77 (dd, J=7.4, 7.4 Hz, 3H), 1.54 (s, 3H), 1.81–1.87 (m, 2H), 7.42–7.43 (m, 1H), 7.47 (m, 1H), 7.57–7.59 (m, 1H), 7.70 (s, 1H) ppm; 13C{1H} NMR (CDCl₃, 125 MHz) δ 8.5, 30.0, 37.0, 75.1, 122.2, 123.7, 124.7 (q, J=270.5 Hz), 128.8, 128.9, 130.8 (q, J=31.8 Hz), 149.1 ppm; IR (NaCl) 3409, 2974, 1613, 1166 cm-1; MS (m/z relative intensity) 218 (M)+ (29), 217 (M-1)+ (78), 200 (M-H2O)+ (10), 185 (12); HRMS calcd for $C_{11}H_{12}$ (—OH)+: 201.0891, found 201.0889.

Example 6

Preparation of 2-(2-Methylphenyl)-2-butanol (5)

The general procedure A was applied to 2-methylacetophenone on a 0.14 mL (1.09 mmol) scale, using 10 mol % of the Compound B enantiomer (60 mg). The crude was purified by column chromatography on silica gel (hexanes/EtOAc: 95/5) to give 5 (44 mg, 24.4% yield, 96.0% ee) as an oil: [α]D 20=+7.0 (c 1.8, CHCl₃).

Example 7

Preparation of 1-Ethyl-1,2,3,4-tetrahydronaphthalen-1-ol (6)

Diethylzinc addition to u-tetralone (133 μL, 1.00 mmol) was performed according to general procedure A using 10 mol % of Compound B (54.7 mg). The resulting oil was purified by column chromatography (hexanes/EtOAc: 96/4) to yield 35% of a yellow oil (>99% ee): [α]D 20=-0.67 (c 2.2, MeOH). [Published [α]D 20=-1.61 (c 2.3, MeOH, 89% ee)].

Example 8

Preparation of 3-Phenyl-3-heptanol (7)

The general procedure A was applied to valerophenone on a 0.15 mL (0.91 mmol) scale, using 10 or 2 mol % of the Compound B enantiomer (50 or 10 mg). The crude was purified by column chromatography on silica gel (hexanes/EtOAc: 95/5) to give 7 (146 mg, 83% yield and 138 mg, 79% yield respectively, 87–88% ee) as an oil: [α]D 20=+2.42 (c 2.2, CHCl₃).

Example 9

Preparation of 1–Chloro-3-phenyl-3-pentanol (8)

Diethylzinc addition to 3-chloropropiophenone (0.5 g, 2.97 mmol) was performed according to general procedure B using 10 mol % of Compound B (162.1 mg). The crude product was filtered through a pad of basic alumina with EtOAc (200 mL) to yield 485 mg of 8 (82% yield, 88% ee) as a colorless oil: [α]D 20=-21.0 (c 3.0, MeOH); 1H NMR (CDCl₃, 360 MHz) δ 0.76 (dd, J=7.6, 7.6 Hz, 3H), 1.76–1.90 (m, 2H), 2.25–2.34 (m, 2H), 3.20–3.29 (m, 1H), 3.48–3.60 (m, 1H), 7.20–7.39 (m, 5H) ppm; 13C{1H} NMR (CDCl₃, 90 MHz) δ 7.55, 36.08, 40.58, 45.46, 77.00, 125.20, 126.92, 128.45, 144.33 ppm; IR (KBr) 3566, 3462, 3087, 3060, 3027, 2969, 2936, 2879, 1602, 1494, 1446, 1340, 1251, 1173, 1124, 1074, 1055, 1031, 1014, 989, 900, 762, 702, 611 cm-1; HRMS calcd for $C_{11}H_{14}Cl$ (—OH)+: 181.0784, found 181.0789 (chlorine splitting pattern observed).

Example 10

Preparation 2-(1–Cyclohexenyl)-2-butanol (9)

Diethylzinc addition to 1-(1-cyclohexenyl)-ethanone (1.04 mL, 8.05 mmol) was performed according to general procedure A using 2 mol % of Compound B enantiomer (88 mg). The product was purified by column chromatography (hexanes/EtOAc: 96/4) to give 697.1 mg of 9 (56% yield, 96% ee) of a colorless oil: [60 ]D 20=+5.9 (c 3.0, MeOH). [Published [α]D 20=+0.7 (c 3.0, MeOH, 51% ee)].

Example 11

Preparation of (1E)-3-Methyl-1-phenyl-1-penten-3-ol (10)

The general procedure A was applied to trans-4-phenyl-3-buten-2-one on a 134 mg (0.91 mmol) scale, using 2 mol % of Compound B (10 mg). The crude was purified by column chromatography on silica gel (hexanes/EtOAc: 95/5) to give 10 (128 mg, 79.7% yield, 90.3% ee) as an oil: [α]D 20=-14.7 (c 1.9, CHCl₃).

Example 12

Preparation of 3-Methyl-1-phenyl-3-pentanol (11)

The general procedure A was applied to 4-phenyl-2-butanone on a 0.16 mL (1.09 mmol) scale, using 10 mol % of Compound B (60 mg). The crude was purified by column chromatography on silica gel (Hexanes/EtOAc: 80/20) to give 11 (132 mg, 67.6% yield, 70.0% ee) as an oil: [α]D 20=-1.7 (c 2.3, CHCl₃); 1H NMR (CDCl₃, 500 MHz) δ 0.93 (dd, J=7.5, 7.5 Hz, 3H), 1.21 (s, 3H), 1.53–1.58 (m, 2H), 1.73–1.77 (m, 2H), 2.65–2.68 (m, 2H), 7.17–7.20 (m, 3H), 7.25–7.28 (m, 2H) ppm; 13C{1H} NMR (CDCl₃, 125 MHz) δ 8.6, 26.7, 30.7, 34.8, 43.6, 73.2, 126.1, 128.7, 128.8, 143.1 ppm; IR (NaCl) 3393, 3025, 1603, 1454, 1147 cm-1; MS (m/z relative intensity) 200 (M+Na-1)+ (32), 165 (18), 164 (15), 159 (M–H2O)+ (12), 145 (8); HMRS calcd for $C_{12}H_{17}$ (—OH)+: 161.1330, found 161.1329.

The invention being thus described, it will be obvious that the same may be modified or varied in many ways. Such modifications and variations are not to be regarded as a departure from the spirit and scope of the invention and all such modifications and variations are intended to be included within the scope of the following claims.

I claim:

1. A compound selected from the group consisting of:

Bicyclo[2.2.1]heptane-1-methanesulfonamide,N,N'-(1S,2S)-1,2-cyclohexanediylbis[2-hydroxy-7,7-dimethyl]-(1R,1'R,2S,2'S,4S,4'S)-(9CI) and Bicyclo[2.2.1]

heptane-1-methanesulfonamide,N,N'-(1R,2R)-1,2-cyclohexanediylbis[2-hydroxy-7,7-dimethyl]-(1S,1'S,2R,2'R,4R,4'R)-(9CI).

2. A method for making a compound selected from the group consisting of: Bicyclo[2.2.1]heptane-1-methanesulfonamide,N,N'-(1S,2S)-1,2-cyclohexanediylbis[2-hydroxy-7,7-dimethyl]-(1R,1'R,2S,2'S,4S,4'S)-(9CI) and Bicyclo[2.2.1]heptane-1-methanesulfonamide,N,N'-(1R,2R)-1,2-cyclohexanediylbis[2-hydroxy-7,7-dimethyl]-(1S,1'S,2R,2'R,4R,4'R)-(9CI), comprising the steps of:
   (a) reducing an enantiomer of 1,2-bis(camphorsulfonamido)-cyclohexane; and
   (b) separating said compound from the reaction mixture and its diastereoisomer.

3. The method of claim 2, wherein the step of reducing said intermediate is carried out at room temperature in a reaction mixture additionally comprising sodium borohydride in a 1:1 mixture of isopropyl alcohol and tetrahydrofuran.

4. The method of claim 2, wherein the step of separating the compound of Formula I from its diastereoisomer is carried out by column chromatography.

5. The method of claim 2, comprising the additional steps, following the step of reducing said intermediate and preceding the step of separating said compound from the reaction mixture and its diastereoisomer, of:
   (i) quenching the reaction mixture; and
   (ii) recovering said compound.

6. A method for making a chiral tertiary alcohol with high enantioselectivity, comprising reacting a metal-alkyl donor compound with a starting ketone compound in the presence of titanium(IV) isopropoxide and a compound selected from the group consisting of:
   Bicyclo[2.2.1]heptane-1-methanesulfonamide,N,N'-(1S,2S)-1,2-cyclohexanediylbis[2-hydroxy-7,7-dimethyl]-(1R,1'R,2S,2'S,4S,4'S)-(9CI) and Bicyclo[2.2.1]heptane-1-methanesulfonamide,N,N'-(1R,2R)-1,2-cyclohexanediylbis[2-hydroxy-7,7-dimethyl]-(1S,1'S,2R,2'R,4R,4'R)-(9CI).

7. The method of claim 6, wherein said metal-alkyl donor compound is dialkylzinc.

8. The method of claim 7, wherein said metal-alkyl donor compound is diethylzinc.

9. The method of claim 6, wherein said starting ketone compound is of Formula II:

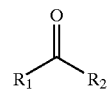

II wherein:
   $R_1$ and $R_2$ are independently selected from the group consisting of straight or branched $C_1$–$C_9$ alkyl, straight or branched $C_2$–$C_9$ alkenyl, straight or branched $C_2$–$C_9$ alkynyl, straight or branched $C_1$–$C_9$ alkyl substituted at one or more positions with Ar, straight or branched $C_2$–$C_9$ alkenyl substituted at one or more positions with Ar, and straight or branched $C_2$–$C_9$ alkynyl substituted at one or more positions with Ar,
   or $R_1$ and $R_2$ are taken together to form a 5–7 membered alicyclic or aromatic, carbo- or heterocyclic ring; and
   Ar is an aromatic, mono-, bi- or tricyclic, carbo- or heterocyclic ring, wherein the ring is optionally substituted with one or more substituent(s) independently selected from the group consisting of alkylamino, amido, amino, aminoalkyl, azo, benzyloxy, $C_1$–$C_9$ straight or branched chain alkyl, $C_1$–$C_9$ alkoxy, $C_2$–$C_9$ alkenyloxy, $C_2$–$C_9$ straight or branched chain alkenyl, $C_3$–$C_8$ cycloalkyl, $C_5$–$C_7$ cycloalkenyl, carbonyl, carboxy, cyano, diazo, ester, formanilido, halo, haloalkyl, hydroxy, imino, isocyano, isonitrilo, nitrilo, nitro, nitroso, phenoxy, sulfhydryl, sulfonylsulfoxy, thio, thioalkyl, thiocarbonyl, thiocyano, thioester, thioformamido, trifluoromethyl, and carboxylic and heterocyclic moieties; wherein each individual alicyclic or aromatic ring contains 5–8 members and wherein each heterocyclic ring contains 1–6 heteroatom(s) independently selected from the group consisting of O, N, and S.

10. The method of claim 9, wherein said starting ketone compound is a straight or branched $C_1$–$C_9$ alkyl ketone, a straight or branched $C_1$–$C_9$ alkyl aryl ketone, or a straight or branched $C_1$–$C_9$ α,β-unsaturated ketone which is optionally substituted with Ar.

11. The method of claim 6, wherein said method comprises the additional step of isolating the resulting chiral tertiary alcohol.

* * * * *